(12) United States Patent
Clement et al.

(10) Patent No.: US 6,605,083 B2
(45) Date of Patent: *Aug. 12, 2003

(54) REDUCTION OF VASCULAR BLEMISHES BY SELECTIVE THERMOLYSIS

(76) Inventors: Robert Marc Clement, 11 Plas Road, Rhos Pontardawe SA8 3HD (GB); Michael Noel Kiernan, 11 Roman Court, Blackpill, Swansea SA3 5BL (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 53 days.

(21) Appl. No.: 09/194,528
(22) PCT Filed: May 23, 1997
(86) PCT No.: PCT/GB97/01411
§ 371 (c)(1), (2), (4) Date: Jul. 14, 1999
(87) PCT Pub. No.: WO97/45163
PCT Pub. Date: Dec. 4, 1997

(65) Prior Publication Data
US 2002/0013578 A1 Jan. 31, 2002

(30) Foreign Application Priority Data
May 29, 1996 (GB) .................................. 9611170

(51) Int. Cl.⁷ .................................. A61B 18/18
(52) U.S. Cl. .................................. 606/17; 606/9; 606/13
(58) Field of Search .................................. 607/88, 89, 90, 607/93; 606/2, 7–19; 372/23

(56) References Cited

U.S. PATENT DOCUMENTS 4,518,232 A * 5/1985 Dagenais .................... 359/853

(List continued on next page.)

FOREIGN PATENT DOCUMENTS

| DE | G02B27/00 | 9/1991 |
|----|-----------|--------|
| EP | 0165060 B1 | 6/1985 |
| EP | 0284330 A1 | 3/1988 |
| EP | 0320080 A1 | 5/1988 |
| EP | 0443033 A1 | 9/1990 |
| EP | 0429297 A2 | 11/1990 |
| NL | 9300064 | 1/1993 |
| WO | WO87/04632 | 8/1987 |
| WO | WO88/00072 | 1/1988 |
| WO | WO91/12050 | 8/1991 |
| WO | WO91/13652 | 9/1991 |
| WO | WO95/19808 | 7/1995 |
| WO | WO96/22813 | 8/1996 |
| WO | WO96/25979 | 8/1996 |

OTHER PUBLICATIONS

"Luminescent Characteristics of Flashlamps for Dye Lasers", by Maeda, Okada, Fujiwara, Uchino, and Miyazoe, Jan. 7, 1975, Kyushu Univ., Fukuoka.

NBS Technical Note 603, "Construction of a Flashlamp-pumped Dye Laser and an Acousto-optic modulator for mode-locking", Jul. 1971, by Jennings and Baldwin.

"Tunable Dye Lasers" by D.J. Bradley, Queen's University, Belfast.

*Primary Examiner*—Rosiland S. Kearney
(74) *Attorney, Agent, or Firm*—Rutan & Tucker LLP; Robert D. Fish

(57) ABSTRACT

Vascular blemishes are reduced by directing pulsed laser radiation to converge toward the blemishes in a plurality of directions, each beam of radiation being derived from a primary radiation source or from a separate radiation source, thereby to cause selective thermolysis of blood vessels in the blemishes.

10 Claims, 2 Drawing Sheets

U.S. PATENT DOCUMENTS

| | | | |
|---|---|---|---|
| 4,733,660 A | | 3/1988 | Itzkan .................... 128/303.1 |
| 4,973,848 A | | 11/1990 | Kolobanov et al. ...... 250/458.1 |
| 5,287,380 A | | 2/1994 | Hsia ........................... 372/69 |
| 5,292,320 A | * | 3/1994 | Brown et al. ................ 606/14 |
| 5,505,726 A | * | 4/1996 | Meserol ........................ 606/9 |
| 5,586,981 A | * | 12/1996 | Hu ................................ 606/9 |
| 5,746,735 A | * | 5/1998 | Furumoto et al. ............. 606/9 |
| 5,746,738 A | * | 5/1998 | Cleary et al. ................ 606/15 |
| 5,807,387 A | * | 9/1998 | Druais ......................... 606/10 |
| 6,379,347 B1 | * | 4/2002 | Maki et al. ................... 606/17 |

\* cited by examiner

REDUCTION OF VASCULAR BLEMISHES BY SELECTIVE THERMOLYSIS

BACKGROUND OF THE INVENTION

1. Field of the Invention

The present invention relates to a method and apparatus for cosmetic reduction of vascular skin blemishes by means of thermolysis using laser irradiation.

2. State of the Art

Vascular irregularities below the surface of the skin can cause visible skin blemishes such as the conditions commonly referred to as Portwine stains, Naevus, Telangiectasia, Strawberry Haemangioma and Thread veins. It has become common practice to cosmetically reduce and preferably remove such vascular blemishes using techniques known as selective thermolysis in which pulsed laser light of a pre-selected wavelength incident on and passing through the skin of a patient is specifically absorbed by a target vascular irregularity lesion leading to "coagulation necrosis" which results in a cosmetic normalising of the colour or tint of the visible blemish with the surrounding skin. Typically a flash lamp pumped dye laser has been utilised emitting light at a wavelength of between 570 nm–600 nm at typical output energy levels of 5–15 $J/cm^2$ with pulse durations in the range 100–600 micro-seconds.

In known selective thermolysis techniques, only a relatively small proportion of the volume of individual blood vessels (depending on the size of the vessels, which can be from 5 microns to 2 mm) comprising the vascular irregularity lesion is heated to thermolysis temperature during the laser pulse. The thermolysis effect is therefore limited to a localised volume of the blood vessels and reduces the probability of the blemish being removed by the treatment.

The present invention seeks to alleviate the above-mentioned difficulty.

SUMMARY OF THE INVENTION

According to a first aspect, the invention provides a method of cosmetically reducing a vascular blemish at or below the surface of mammalian skin, which method comprises directing laser radiation to converge toward said blemish from a plurality of different directions, thereby to cause selective thermolysis of blood vessels comprising said vascular blemish.

Because the vessels comprising the blemish are below the surface of the skin, the directed laser radiation is arranged to converge below the surface of the skin. Irradiating the vascular blemish from a plurality of different directions rather than from a single direction only (usually normal to the skin) as with conventional thermolysis techniques, causes a larger volume of individual vessels comprising the vascular blemish to be heated, thereby increasing the average vessel temperature and hence increasing the likelihood of complete or substantial removal of the blemish.

It is preferred that a plurality of substantially linear paths of radiation are provided, each preferably comprising a separate beam, being arrange to converge toward the vascular blemish. Preferably the respective paths or beams are angularly spaced relatively to one another. Desirably, one of the beams or paths is directed normally to the skin of the patient at least one further beam or path being directed at an inclined angle relative to the skin of the patient.

Advantageously, the laser radiation is directed to converge from the plurality of different directions effectively simultaneously. Desirably the directed radiation is pulsed preferably having a pulse duration in the range 100 to 600 micro-seconds.

In a first embodiment of method according to the invention, the laser radiation may comprise a primary beam which is split into a plurality of individual beams which are subsequently directed to converge on the vascular blemish. Alternatively, separate beams may be used, each from a separate source.

It is preferred that the laser radiation converging from the plurality of directions is of the same wavelength (and preferably the same intensity) from each direction. Each of the converging laser beams are therefore effectively identical.

According to a second aspect of the invention, there is provided a laser apparatus for use in selective thermolysis techniques, the apparatus comprising means for directing a laser radiation to converge from a plurality of different directions at a zone of convergence spaced from the apparatus.

It is preferred that the apparatus is arranged to produce a plurality of beams each directed along a respective substantially linear path, the beams being angularly spaced from one another to converge at the zone of convergence.

Advantageously, the beams are arranged to be of substantially the same wavelength, and also preferably of substantially the same intensity.

In one embodiment, apparatus according to the invention may comprise division means for dividing the plurality of laser beams from a primary beam. The division means preferably comprises optical means which may include mirrors and/or beam splitters and/or optical prisms. Desirably, focusing means is provided to focus each beam at the convergence zone. Typically the focusing means comprises a focusing lens.

It is preferred that in certain embodiments modification means is provided to modify the configuration of the beams for example by providing that the focusing means is arranged to focus the respective beam to a line rather than a point or spot. An at least partially cylindrical optic lens is preferably provided for this purpose.

It is believed that laser apparatus for use in selective thermolysis techniques and comprising focusing means arranged to focus a laser beam to a line is inventive per se. This is particularly useful where the target blemish for photothermolysis is substantially linear such as, for example, a thread vein.

In an alternative embodiment, the apparatus may comprise discrete laser sources arranged to produce each respective laser beam.

In either embodiment, it is preferred that pulsation means is provided to pulse the laser radiation.

Specific embodiments of the invention will now be further described by way of example only, and with reference to the accompanying drawings.

DETAILED DESCRIPTION OF THE PREFERRED EMBODIMENTS

Figure 1:
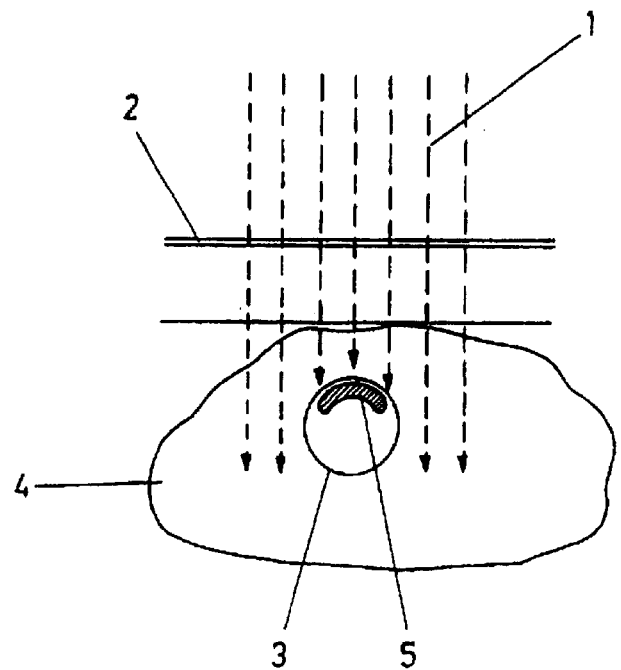
FIG. 1 is a schematic representation of a prior art photothermolysis technique.

Referring to FIG. 1, prior art thermolysis techniques utilise a uni-directional beam 1 of laser radiation aimed in a direction substantially normal to the surface of the skin 2 and impinging on a sub-cutaneous blood vessel 3 comprising a general region 4 of vascular irregularity such as a Portwine stain, Strawberry Haemangioma or the like. The laser radiation incident on vessel 3 heats a relatively small peripheral volume 5 of the vessel to the thermolysis temperature which leaves a substantial volume of the vessel insufficiently heated and therefore the vascular blemish is not entirely removed.

Figure 2:
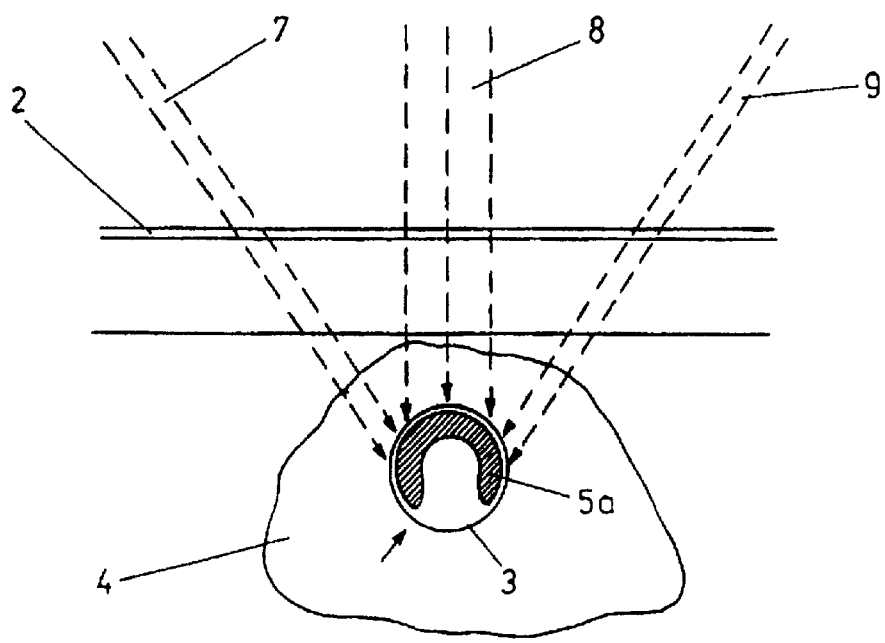
FIG. 2 is a schematic representation of the method according to the invention.

Referring to FIG. 2, the technique according to the invention utilises three discrete beams 7, 8, 9 of laser radiation passing through the surface of the skin 2 at different inclinations and arranged to converge on vessels 3 in the region 4 of the vascular irregularity. This has the benefit of ensuring that a larger peripheral volume 5a of the vessel 3 is heated to thermolysis temperature and thereby ensures more complete removal of the vascular blemish. Furthermore, because the beams 7, 8, 9 of radiation are superposed only in the region 4 of the vascular irregularity, the high intensity needed for thermolysis is restricted to that region because each individual beam may be of lower intensity radiation. This prevents over heating and thermal damage being caused to tissue outside region 4. As a corollary, it is possible to have a higher intensity of radiation in the region 4 than is the case with conventional single beam thermolysis techniques due to the effect of superposition.

Figure 3:
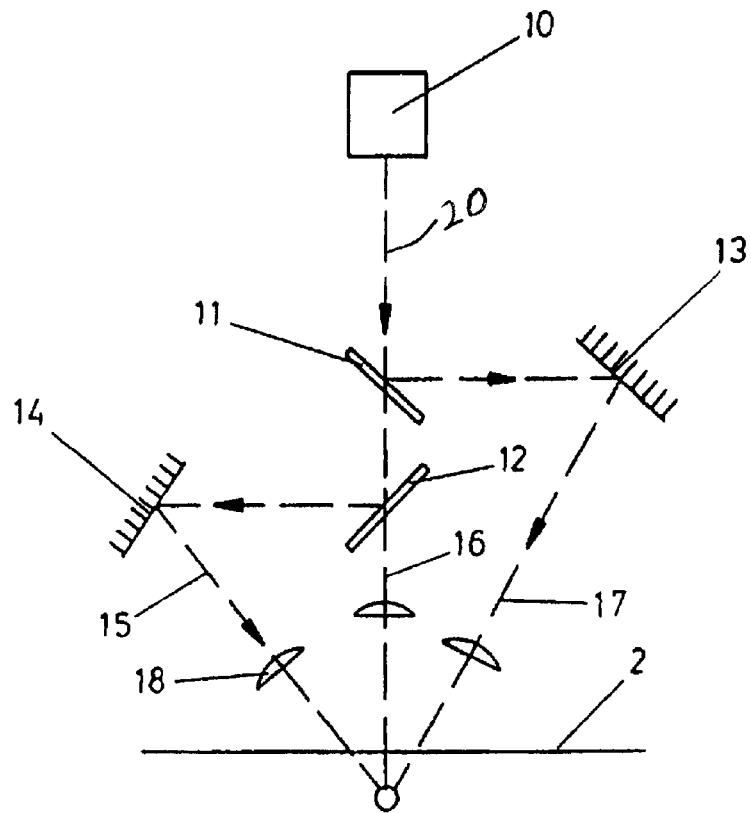
FIG. 3 is a schematic representation of an embodiment of apparatus according to the invention.

FIG. 3 shows apparatus suitable for use in reducing a vascular blemish in accordance with the invention. The apparatus comprises a laser source 10, beam splitters 11, 12 (each arranged to transmit 66% and reflect 33% of incoming radiation) and mirror reflectors 13, 14 arranged to divide the primary beam 20 into three beams 15, 16, 17 which are focused by lenses 18 to converge below the surface of the skin 2.

Figure 4:
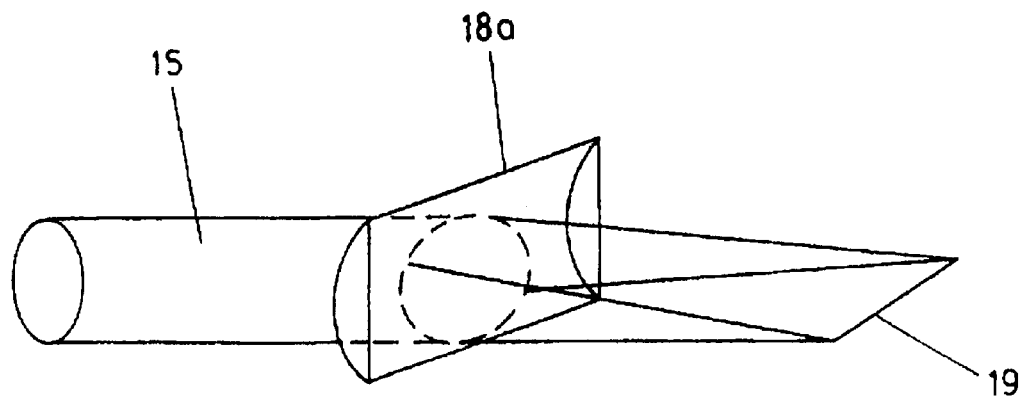
FIG. 4 is a schematic representation of a component suitable for use in an embodiment of the apparatus of FIG. 3.

In an embodiment of the apparatus, the beams 15, 16, 17 may be modified by means of a cylinder optic lens 18a (shown in FIG. 4) to produce a line of focus 19 rather than a point or spot as with conventional optics. This is particularly useful for use in removing elongate blemishes such as thread veins.

What is claimed is:

1. A blemish reducer, comprising:
   a laser source that produces a beam of laser radiation; and
   a focusing mechanism arranged to focus the beam to produce a linear pattern of focused laser radiation on a blemish, even when the beam is not being drawn across the blemish.

2. The blemish reducer of claim 1, wherein the focusing mechanism comprises a focusing lens.

3. The blemish reducer of claim 2, wherein the focusing lens is an optic lens.

4. The blemish reducer of claim 3, wherein the optic lens is at least partially cylindrical.

5. The blemish reducer of claim 1, which includes a pulsation mechanism arranged to pulse the beam of laser radiation.

6. A method of thermolyzing and reducing a blemish comprising:
   providing a laser source that produces a beam of laser radiation;
   providing a focusing mechanism; and
   directing the beam of laser radiation towards the focusing mechanism to produce a linear pattern of focused laser radiation on the blemish, even when the beam is not being drawn across the blemish.

7. The method of claim 6, wherein the beam of laser radiation is a pulsed laser beam.

8. The method of claim 7, wherein the pulsed laser beam has pulses of duration in the range 100 to 600 microseconds.

9. The method of claim 6, wherein the blemish comprises an elongate vascular blemish.

10. The method of claim 9, wherein the elongate vascular blemish comprises a thread vein.

* * * * *